(12) United States Patent
King et al.

(10) Patent No.: US 9,398,769 B2
(45) Date of Patent: Jul. 26, 2016

(54) BROMATE SUPPRESSION

(71) Applicants: Joseph A King, Wayzata, MN (US); John Hill, Plymouth, MN (US)

(72) Inventors: Joseph A King, Wayzata, MN (US); John Hill, Plymouth, MN (US)

(73) Assignee: KING TECHNOLOGY, INC, Hopkins, MN (US)

( * ) Notice: Subject to any disclaimer, the term of this patent is extended or adjusted under 35 U.S.C. 154(b) by 548 days.

(21) Appl. No.: 13/694,044

(22) Filed: Oct. 23, 2012

(65) Prior Publication Data

US 2014/0113003 A1 Apr. 24, 2014
US 2016/0174563 A9 Jun. 23, 2016

Related U.S. Application Data

(62) Division of application No. 12/386,074, filed on Apr. 14, 2009, now abandoned.

(60) Provisional application No. 61/126,136, filed on May 1, 2008.

(51) Int. Cl.
| | |
|---|---|
| *A01N 59/16* | (2006.01) |
| *C02F 1/50* | (2006.01) |
| *C02F 1/68* | (2006.01) |
| *C02F 1/76* | (2006.01) |
| *C02F 1/78* | (2006.01) |
| *A61L 2/00* | (2006.01) |
| *A61L 9/00* | (2006.01) |
| *C02F 103/42* | (2006.01) |

(52) U.S. Cl.
CPC . *A01N 59/16* (2013.01); *A61L 2/00* (2013.01); *A61L 9/00* (2013.01); *C02F 1/505* (2013.01); *C02F 1/688* (2013.01); *B01D 2257/2062* (2013.01); *C02F 1/685* (2013.01); *C02F 1/766* (2013.01); *C02F 1/78* (2013.01); *C02F 2103/42* (2013.01); *C02F 2303/185* (2013.01)

(58) Field of Classification Search
CPC ............. A01P 8/00; A01N 59/16; C02F 1/50; C02F 1/505; C02F 1/766; C02F 1/78; C02F 2303/04; C02F 2303/185; C02F 2103/42; C02F 1/685; C02F 1/687; C02F 1/688; B01J 8/00; B01F 2001/0061; A61L 2/00; A61L 9/00; B01D 2257/2062
See application file for complete search history.

(56) References Cited

U.S. PATENT DOCUMENTS

| | | | | |
|---|---|---|---|---|
| 4,749,537 A | * | 6/1988 | Gautschi et al. | 264/232 |
| 5,888,428 A | * | 3/1999 | Howarth et al. | 252/403 |
| 2006/0043011 A1 | * | 3/2006 | King et al. | 210/198.1 |
| 2009/0272698 A1 | * | 11/2009 | Hill et al. | 210/754 |

* cited by examiner

*Primary Examiner* — Lucas Stelling
(74) *Attorney, Agent, or Firm* — Jacobson & Johnson LLC

(57) ABSTRACT

A apparatus and method for killing microorganisms in a body of water that has been treated with ozone in the presence of bromide ions with the method comprising the steps of carrying out the ozonization of a body of water in the presence of bromide ions, adding a metal ion donor to the body of water, and adding a hypobromite ion scavenger to the body of water to interact with the metal ion donor to enhance a metal ion concentration in the body of water while suppressing the oxidization of the bromide by the Ozone to produce bromate.

5 Claims, 4 Drawing Sheets

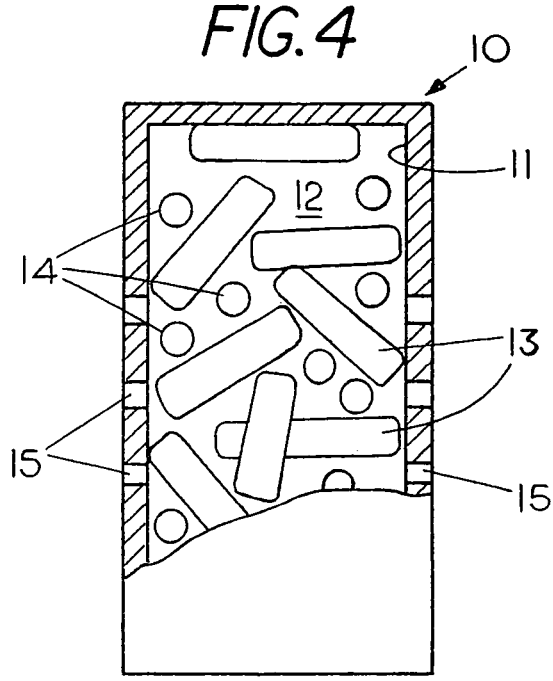
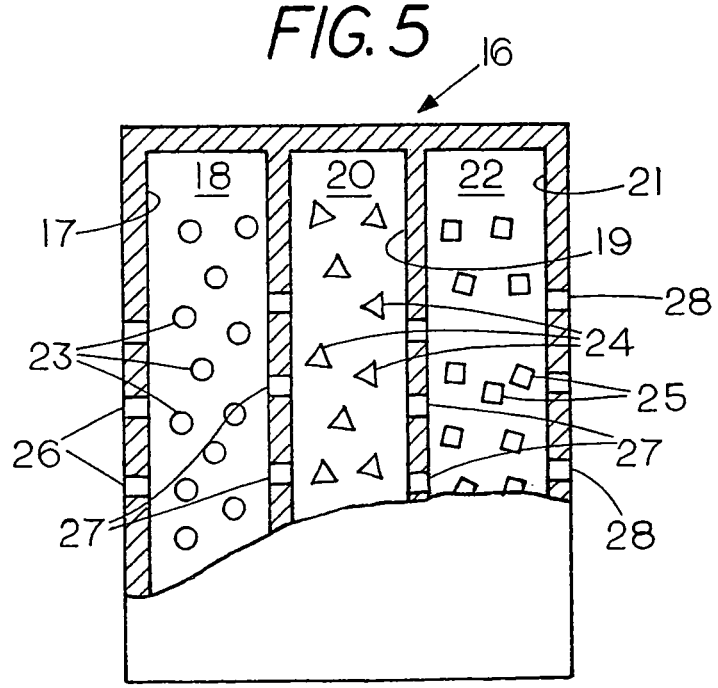

BROMATE SUPPRESSION

CROSS REFERENCE TO RELATED APPLICATIONS

This application is a divisional application of Ser. No. 12/386,074 filed Apr. 14, 2009 titled BROMATE SUPPRESSION, which claims priority to Provisional Application Ser. No. 61/126,136; filed on May 1, 2008; titled ION ENHANCEMENT AND BROMATE.

FIELD OF THE INVENTION

This invention relates generally to water treatment and more specifically, to the combination of a metal ion donor, bromide ion donor and a source of a hypobromite ion scavenger such as dimethylhydantoin (DMH) to enhance the effectiveness of the metal ion donor in kill microorganisms in a body of water that has been treated with ozone while eliminating or reducing the production a bromate.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of treating water with a source of metallic ions to kill bacteria in a body of water is known in the art. A metallic ion such as a silver ion is an effective bactericide for a body of water including recreational water such as swimming pools, spas, jetted tubs or the like and is a preferred material because it is generally easier and safer to use when compared to other known bactericides or algaecides. A further advantage of using silver ion as a bactericide is that silver ion minimizes the need for pH adjustment to the body of water. However, if the concentration of metallic ions such as silver ions in a body of water is too low the ability to kill microorganisms is reduced or lost. Conversely, if the concentration of metallic ions such as silver ions is too high it can potentially lead to undesired effects such as causing the user's skin to turn yellow and staining clothes. Thus when silver ion is used as a disinfectant in a body of water one generally want to maintain the concentration of the silver ion in a range that is effective killing microorganisms without leading to the undesired effects associated with higher levels of silver ions.

Traditionally, the sources of metallic ions used to kill bacteria in recreational water have been limited to metallic ion donors that are readily soluble in the recreational water in order to maintain an effective concentration of the biocides in the body of water. Silver chloride (AgCl), for example, has been a commonly used bactericide for releasing silver ions into the body of water to effectively kill microorganisms. Sodium bromide has also been known to be used with silver chloride to provide an additional and alternative water disinfection system.

One of the problems associated with the use of silver for killing microorganisms is that silver has a tendency to complex with other compounds and become increasingly insoluble thereby reducing the effective microorganisms killing ability of the silver. For example, it would not be anticipated that silver chloride when used in combination with sodium bromide would be an effective prolonged disinfectant system because of the combination's tendency to form insoluble silver bromide crystals, which are not believed to be biologically active in aqueous environments.

The use of Ozone ($O_3$) for water disinfection is also known in the art. Examples of current Ozone uses include treatment of recreational waters and treatment of wastewater. Use of Ozone for water disinfection is generally preferred because it is considered to be an environmentally-friendly biocide that produces no hazardous by-products when used alone. However, Ozone generally cannot be used alone as an effective prolonged bactericide for a body of water including recreational waters such as swimming pools, spas, jetted tubs or the like because Ozone tends to be unstable in water especially at elevated pH, and it is readily volatilized from water.

To overcome the problems associated with the use of Ozone while retaining the benefits of Ozone usage, it is also known in the art to post-treat water that has been treated with Ozone with a more stable biocide. For example, bromine displays excellent biocidal properties even at elevated pH where Ozone is unstable, and is less prone to volatilization from water than Ozone. The use of a source of bromine such as sodium bromide to post-treated water that has gone through the ozonization process is advantageous in that sodium bromide normally requires a strong oxidizer such as ozone in order to transform sodium bromide into the bromine's biocidially active form. The benefit of the dual use of Ozone and a more stable biocide such as bromine is that use of the Ozone requires less amounts of bromine to be used in order to maintain effective levels of water disinfection.

Although the dual use of Ozone and bromide is effective at maintaining an effective level of water disinfection, the problem associated with the dual use of Ozone and bromide is that the bromides contained in the water are partly oxidized by the Ozone to produce bromate, which is highly undesirable in that bromate, in higher concentrations, is a known carcinogenic.

To solve the above problems, it has been discovered that the introduction of small amounts of hydantoins to a body of water that has been treated with Ozone and containing silver ion and bromide ions results in the silver ions forming a complex with the hydantoins and remain soluble to a higher degree thereby retaining the silver's antimicrobial activity compared to the use of silver ion and bromide ions alone. It has also been determined that the hydantoins functions to suppress the oxidization of the bromide by the Ozone to produce bromate.

The present invention includes a device and method for using metal ion donors and bromide ion donors in combination with hydantoins including unhalogenated hydantoins such as 5,5-dimethylhydantoin (hereinafter "DMH") in a body of water to enhance a concentration of the metal ions in the body of water or to enhance the solubility of metal ions from other metal ion donors to retain the silver's antimicrobial activity in the water while suppressing the oxidization of the bromide by the Ozone to produce bromate.

SUMMARY OF THE INVENTION

Briefly, the present invention comprises a method and a device for killing microorganisms in a body of water that has been treated with ozone in the presence of bromide ions. The apparatus comprises a dispenser with a first housing having a water accessible compartment containing a source of a hypobromite ion scavenger for releasing the hypobromite ion scavenger when contacted by the body of water and a second housing having a water accessible compartment containing a metal ion donor for releasing metal ions when contacted by the body of water. The dispenser may also include a third housing having a water accessible compartment containing a bromide ion donor for releasing bromide ions when contacted by the body of water.

The method includes the steps of carrying out the ozonization of a body of water in the presence of bromide ions, adding a metal ion donor to the body of water, and adding a hypobromite ion scavenger to the body of water to interact with the metal ion donor to enhance a metal ion concentration in the body of water while suppressing the oxidization of the bromide by the Ozone to prevent or reduce the production of bromate.

BRIEF DESCRIPTION OF THE DRAWINGS

FIG. 4 shows a dispenser having a housing containing a compartment containing DMH and a silver ion donor comprising silver chloride therein; and FIG. 5 shows a dispenser having a first housing containing DMH and a second housing containing silver ion donor comprising silver chloride, and a third housing containing a bromide ion donor therein.

DESCRIPTION OF THE PREFERRED EMBODIMENT

Figure 1:
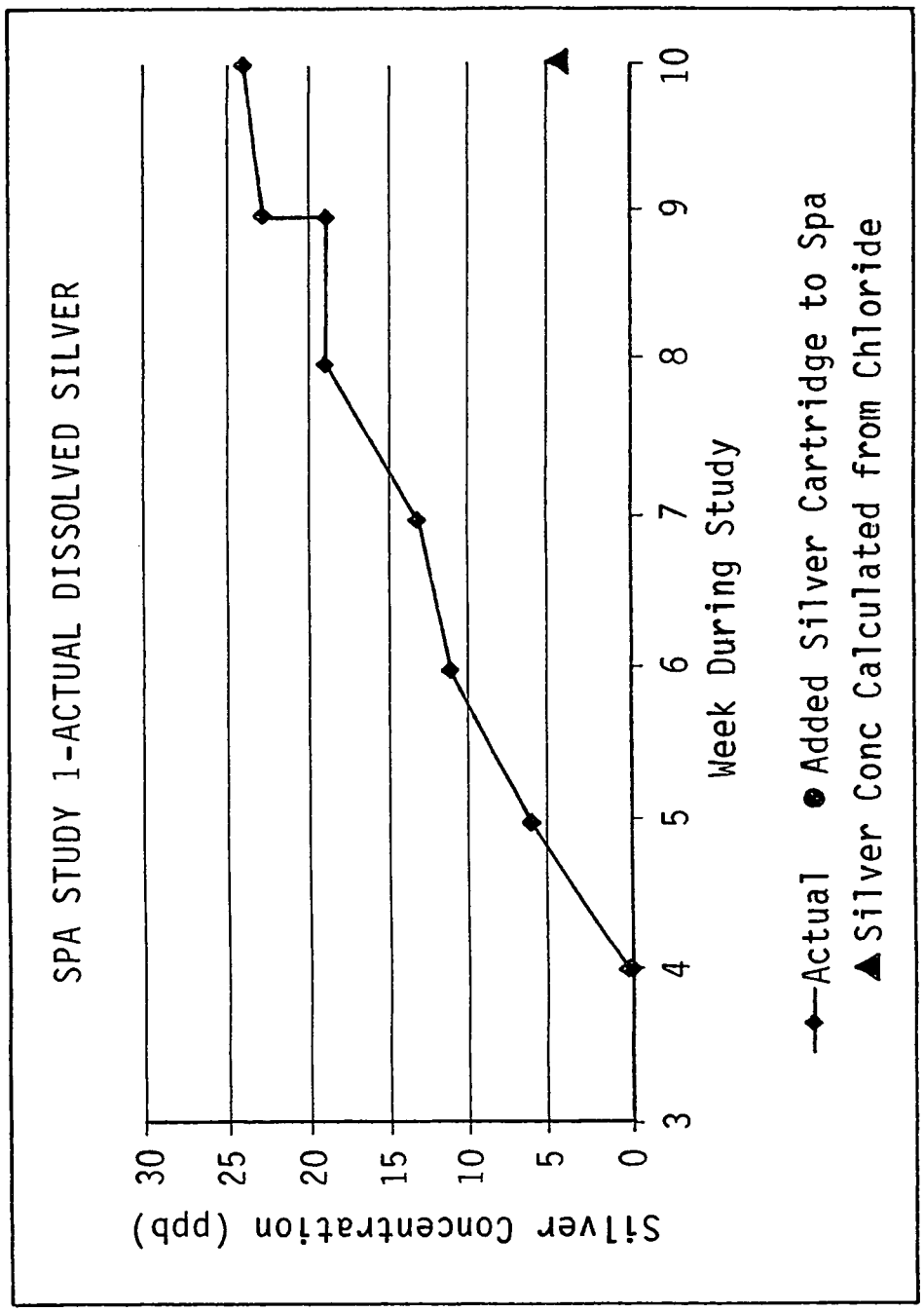
FIG. 1 shows a table containing test results for bromide and dissolved silver concentration for a Spa Study 1.

Hydantoin structures are known complexing agents in silver-plating processes (R. J. Morrissey, U.S. Patent Application Publication no. 2005/0183961). Studies performed by the inventor have demonstrated that halogenerated hydantoins such as Bromochlorodimethylhydantoin (BCDMH) and Dichlorodimethylhydatoin (DCDMH) tend to increase levels of dissolved silver. While not fully understood it is believed that the aforementioned increase in solubility is due to the soluble complex between silver and hydantoin ring structures as it has been found the silver remains soluble to a higher degree than expected.

The present invention has found that unhalogenerated hydantoins, such as 5,5-dimethylhydantoin (DMH), also has the qualities to interact with metal ion donors including silver metal ion donors such as silver bromide to increase the solubility of the silver bromide in a water environment and aid in the disinfection process. That is, with a silver ion donor in the presence of DMH, it has been discovered that the dissolved silver concentrations are higher than anticipated when compared to a control solution without the presence of DMH. The results suggested that DMH interacts with silver to form a soluble complex even if the source(s) of silver are from insoluble salts such as silver bromide, which in some cases may be derived from silver chloride.

The inventor has determined that the introduction of hydantoins to the body of water that has been treated with Ozone and containing silver ion and bromide ions increases the solubility of extremely insoluble silver while suppressing the oxidization of the bromide by the Ozone to reduce or eliminate the production of undesired bromate. In order to verify that the DMH interacts to increase the solubility of extremely insoluble silver, the following test was performed using either silver chloride or silver bromide as the donor of metal ions in order to demonstrate the enhancement of a silver concentration in a body of water when DMH is used in combination.

Testing for Effect of Hydantoins on Silver

Two spas were used in performing three (3) tests to evaluate the potential use of DMH to increase silver solubility in the presence of alternative disinfection systems such as sodium bromide. The first spa used was a 125-gallon Marquis® brand triangle shaped spa having the dimensions 60"×60"×82" with a height of 32" and a water depth of 27" without bathers. This spa featured 13 jets and one pleated filter cartridge (Unicel® 5CH-502), having a filtration area of 50 square feet. The second spa was a 325-gallon Dimension One® brand spa having the dimensions 90"×90"×355" with a water depth of approximately 25" without bathers. The Dimension One® brand spa featured 32 jets and two pleated filter cartridges (Unicel® 7CH-975), each having a filtration area of 75 square feet. Spa water was maintained between 100° F. (37.8° C.) to 104° F. (40° C.) and was circulated at least 2 hours daily.

In the each of the tests a reagent grade Dimethylhydantoin (DMH, CAS No. 77-71-4) obtained from Aldrich® with a 97% purity was used. A concentration of 5 ppm (parts per million) DMH was selected because 5 ppm was the amount of DMH that can be delivered in the existing King Technology, Inc. Spa Frog® Mineral Cartridge to a 600 gallon spa, the largest volume for the cartridge was designed.

The source of silver ions was obtained from a King Technology Inc. Spa Frog® Mineral Cartridge, which was randomly selected from King Technology Inc.'s production inventories for use in these tests and installed into the in-line system on the spa. These mineral cartridges release silver ions into the spa in the form of silver chloride. Although silver chloride is described above as providing for the source of silver ion, in the present embodiment the source of silver ion may also comprises pure silver, silver metals, silver alloy or some combination thereof because of the recognized bactericidal, viricidal, and algaecidal properties of silver. The silver metals can be introduced as metallic, zero valence material, or as metal ions that can be introduced into the water by dissolution of soluble metal salts, or by the dissolution of the metal itself. For example, silver ion can be introduced into the water through the dissolution of silver nitrate, or through the dissolution of metallic silver as the result of conversion to silver oxide and subsequent conversion of the oxide to more soluble silver species. Mixtures of different salts, or of salts with metallic material, may be combined together to provide the necessary concentration of metal ions in the water.

In Spa Studies 1 and 2, a commercially available sodium bromide disinfectant system (Rendezvous®) was used. With the Rendezvous®) bromine disinfectant system, the sodium bromide solution is oxidized by the addition of potassium peroxymonosulfate.

For Spa Study 3, different sodium bromide disinfecting systems were evaluated in two (2) phases. During the first phase, the commercially available sodium bromide oxidized by the sodium dichloro-s-triazinetroine disinfectant known as Spa Essentials® Brominating Concentrate was used. For the second phase of the spa study reagent grade sodium bromide salt and potassium peroxymonosulfate was used.

Addition of DMH

During the study, the spa was filled with fresh water prior to the initiation of each study and the water balanced according to Taylor Technologies Pool & Spa Water Chemistry Manual. The pH was reduced through the addition of sodium bisulfate (pH Down Balancer, GLB, Alpharetta, Ga.) to a range from 7.2 to 8.0. After balancing the spa water the King technology, Inc. Spa Frog® Mineral Cartridge was installed into the inline system of the spa and a source of bromine was added to the spa water.

In Spa Study 1 an amount of DMH was added to the spa water after seven (7) weeks of silver data had been collected to result in a final concentration of 5 ppm (parts per million). For Spa study 2, an amount of DMH was added to the spa water after three (3) weeks of silver data had been collected to result in a final concentration of 5 ppm, and for Spa Study 3 an amount of DMH was added to the spa water after one (1) week of silver data had been collected to result in a final concentration of 5 ppm.

Sodium bromide or brominating concentrate (dichloro-striazinetrione plus sodium bromide) was added to each spa during test intervals. Typically, sodium bromide was activated by oxidation to bromine with potassium peroxymonosulfate. Alternatively, when the brominating concentrate (dichloro-striazinetrione plus sodium bromide) was used, the sodium dichloro-s-triazinetrione oxidized the sodium bromide to make bromine in-situ. Additional water was added to the spa when the water level dropped below the skimmer water returns.

Water Testing

Figure 2:
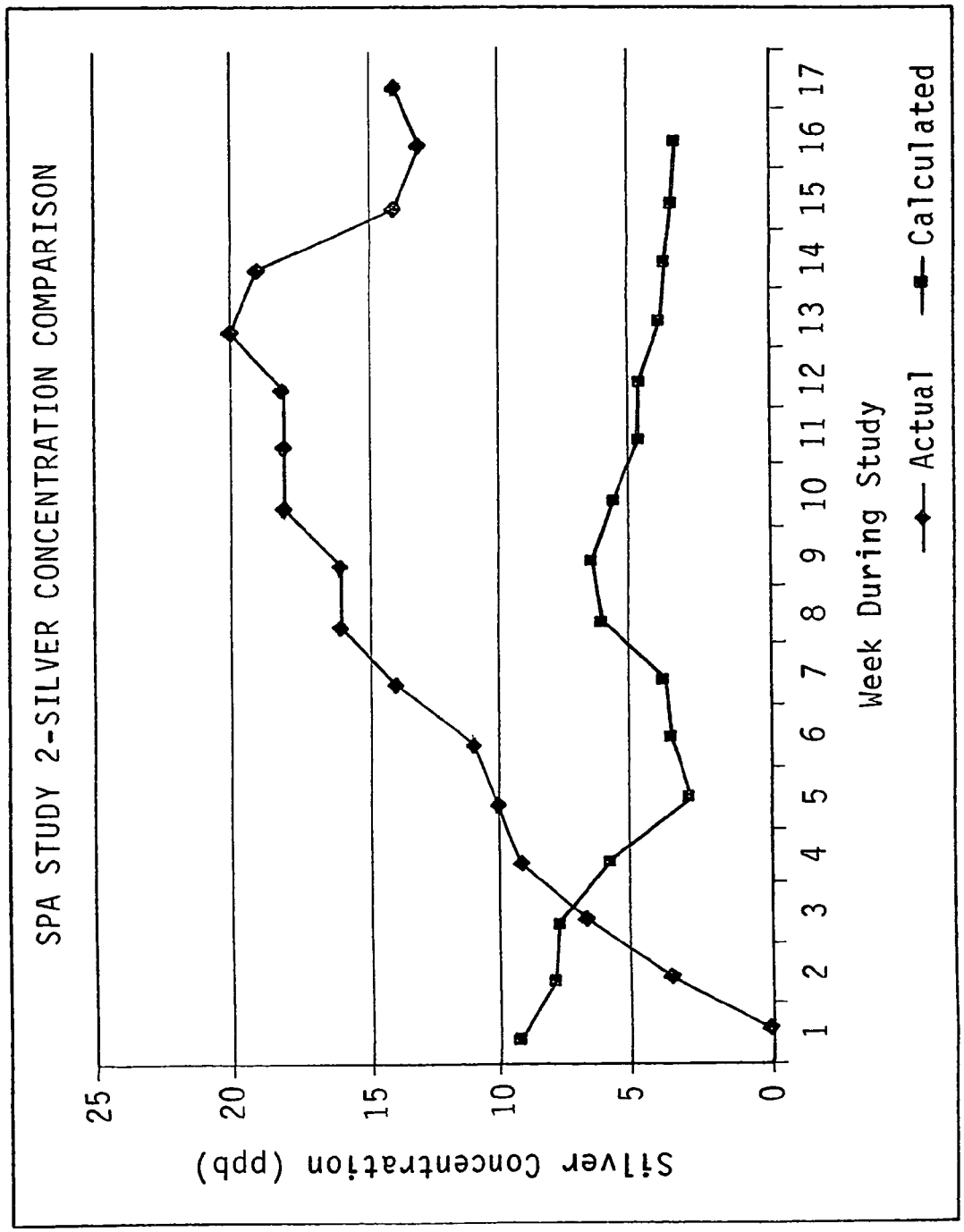
FIG. 2 shows a table containing test results for bromide and dissolved silver concentration for a Spa Study 2.
Figure 3:
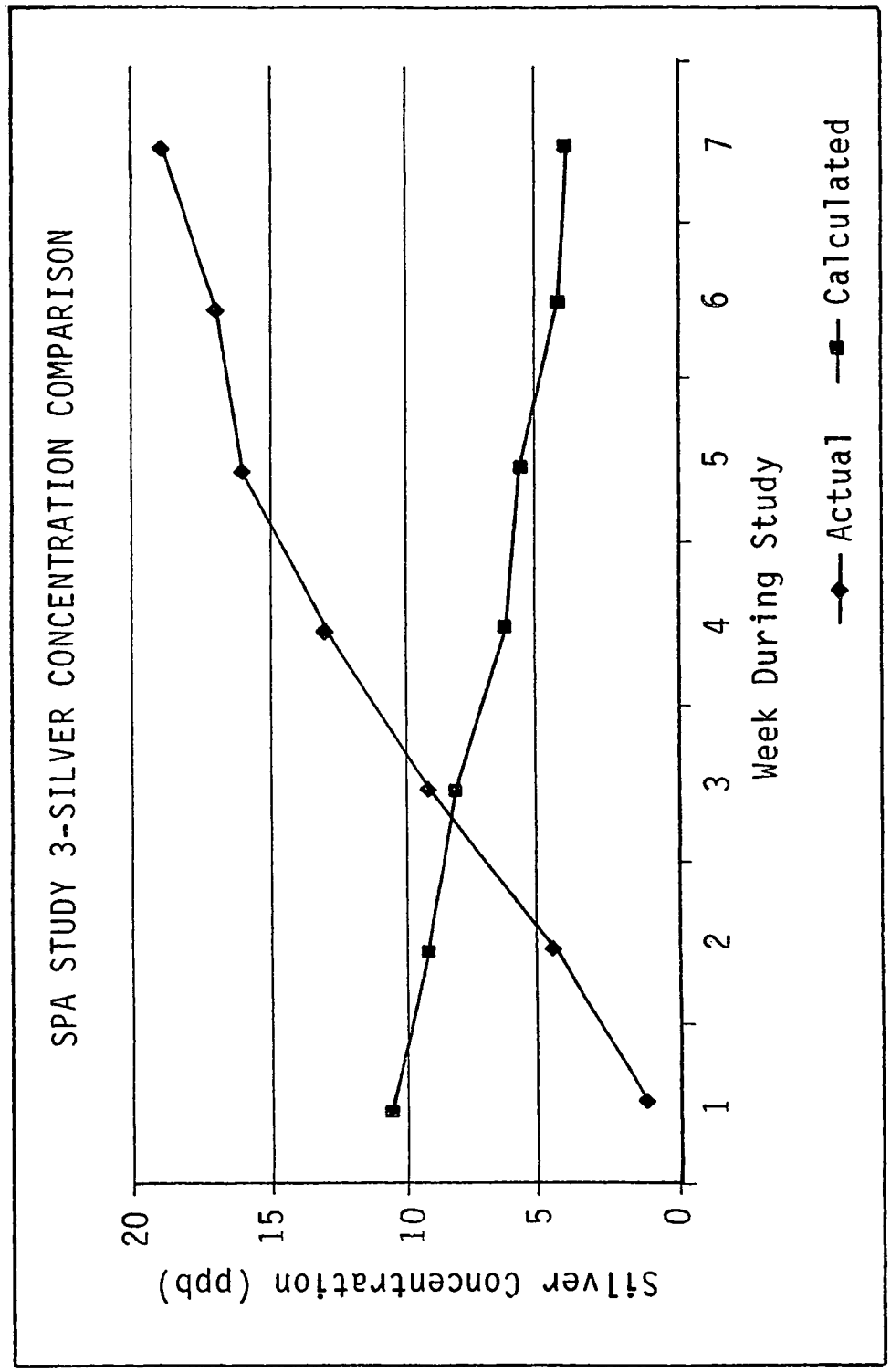
FIG. 3 shows a table containing test results for bromide and dissolved silver concentration for a Spa Study 3.

Chemical tests were performed with water samples obtained from each of the spas for levels of dissolved silver concentration, bromide, and chloride approximately once a week. Bromide was tested to provide a means to calculate the theoretical silver concentration based on the solubility product of silver bromide. Result of the test for bromide and dissolved silver concentration are shown in FIG. 1 for Spa Study 1, are shown in FIG. 2 for Spa Study 2, and are shown in FIG. 3 for Spa Study 3.

Additionally, the spa water's total alkalinity, turbidity, and pH were also tested and maintained within ranges accepted by the industry. The ideal pH for a spa is 7.20 to 7.60, however wider ranges are acceptable. In the studies, the average pH for Spa Study 1 was 7.51, Spa Study 2 showed an average pH of 7.61, and Spa Study 3 had an average pH of 7.47. These three spa studies were maintained within the ideal pH for a spa.

The International Aquatic Foundation (ANSI/NSPI) recommends a level of total bromine to be between 2.0 and 4.0 ppm for residential spas with a max of 6.0 ppm. In the studies, the average total bromine concentration measured for Spa Study 1 was 3.74 ppm, the average total bromine concentration measured for Spa Study 2 was 656 ppm, and the average total bromine concentration measured for Spa Study 3 was 3.58 ppm.

In regards to the level of silver ions, the King Technology, Inc. Spa Frog® Mineral Cartridge contains silver ions in the form of solid silver chloride (AgCl) distributed over a porous matrix. Water flowing through the matrix comes into contact with the silver chloride resulting in the release of soluble silver ions to the water. DMH was also released into the water resulting in the formation of ionic-hydantoin structures. It would be anticipated that soluble silver ions would be depleted from spa water through the formation of silver bromide, an insoluble salt. However, as shown in FIG. 1 for Study 1, after the DMH was added to the water in the pool, the actual silver concentrations were higher than the calculated theoretical silver concentration.

The result of Study 1 were further supported in Study 2 and Study 3, shown in FIGS. 2 and 3, which both show that after the DMH was added to the water in the pool, the actual silver concentrations were higher than the calculated theoretical silver concentration. More specifically, once measurable within reporting limits the average measured concentration of dissolved silver for Spa Study 1 was 55 ppb. Spa Study 2 had an average measured concentration of 5.33 ppb for dissolved silver and Spa Study 3 had a measured concentration of dissolved silver of 32 ppb. Referring to FIGS. 1, 2, and 3, the highest observed silver concentration in each spa study was, 7 ppb; 6 ppb, and 6.5 ppb, respectively.

Referring to FIGS. 1, 2, and 3, the results of the three spa studies revealed that before the addition of DMH, dissolved silver concentration for each of the studies were below the official reporting limit of 4.8 ppb (parts per billion). However, around one to three weeks after the addition of a concentration of 5 ppm DMH, silver concentrations in each of the Spa Studies increased above the reporting limit, and were significantly higher than concentrations that would be anticipated based on silver solubility calculations from silver bromide. The above results of Spa Studies 1, 2, and 3 thus supports the finding that the combination of an unhalogenated hydantoin such as 5,5-dimethylhydantoin with a metal ion donor such as silver bromide enhances a concentration of the metal ions in the body of water by retaining or increasing the solubility of metal ions from other metal ion donors to retain the antimicrobial activity of the metal ions in the water.

Effect of Hydantoins on Silver Interaction between Ozone and Bromide

In regards to the interaction between Ozone and bromide ion, the mechanism for the interaction between Ozone and bromide ion has been well documented by W. R. Haag and J. Hoigne in the article titled "*Ozonization of Bromide-Containing Waters: Kinetics of Formation of Hypobromous Acid and Bromate,*" *Environ. Sci. Technol.*, 17(5), 261, 1983. Referring to the Haag and Hoigne reaction mechanism, which is listed below, it is known that the presence of the bromide ion ($Br^-$) in water that has been ozonized initially results in the formation of hypobromous acid (HOBr), which can function as a secondary biocide. That is, the primary disinfection of the water is accomplished by Ozone, which kills the initial microbial populations. The hypobromous acid then provides for secondary disinfection by killing a lower microbial populations acquired by the water after the initial disinfection of the water by the Ozone

$$O_3 + Br^- \rightarrow HOBr + O_3 \rightarrow O_2 + OBr^- \qquad (1)$$

$$2O_3 + OBr^- \rightarrow 2O_2 + BrO_3^- \qquad (2)$$

As shown in step (1), the exposure of the hypobromous acid to Ozone results in the conversion of the hypobromous acid to hypobromite ($OBr^-$) As shown in step (2), the exposure of the hypobromite ($OBr^-$) to Ozone results in the conversion of the hypobromite ($OBr^-$) to the highly undesirable bromate ion ($BrO_3^-$). On prolonged exposure to Ozone, all the bromide ions will be converted to bromate.

In order to eliminate or reduce the formation of the bromate to a safe level in the body of water, the Inventor has determined that the introduction of small amounts of hypobromite ion ($OBr^-$) scavengers to the water being treated with Ozone and containing bromide ions and silver ions for the purpose of disinfection will result in the suppression of the second step of the Haag and Hoigne reaction mechanism thereby eliminating the formation of the bromate or at the very least reducing the formation of the bromate to a safe level or safe concentration.

In regard to the hypobromite ion scavenger, ideally the hypobromite ion scavenger should possesses a functional group that is capable of intercepting $OBr^-$ ions and preferentially forming some sort of biocidal derivatives. It has been determined that hydantoins such as dimethylhydantoin (DMH) in sufficient amount should be able to suppress the second step of the Haag and Hoigne reaction mechanism, and more specifically suppress the catalytic decomposition reaction of Ozone with hypobromite ions since DMH include the presence of an amide group that would be capable of intercepting the hypobromite ion ($OBr^-$).

The amount of hydantoins required to suppress the catalytic decomposition reaction of Ozone with hypobromite ions depends on the water being treated and on the amount of bromide ions present. An example of one logical type of hydantoin that may be use as an $OBr^-$ ion scavenger additive would be dimethylhydantoin (DMH) as DMH include the presence of an amide group that would be capable of intercepting the hypobromite ion ($OBr^-$). As such, the introduction of hydantoins to the body of water that has been treated with Ozone and containing silver ion and bromide ions provides the dual purpose of (1) not only enhancing the concentration of silver ion for water disinfection but also (2) suppressing the oxidization of the bromide by the Ozone to eliminate or reduce the production the bromate to a safe level for human use.

The present invention provides an enhanced method and system for treating water that has been treated with Ozone and containing silver ion and bromide ions. The additives of the present invention may be readily used with existing ozonization systems. In addition, a source bromide ion, a source of silver ion and the hypobromite ion scavenger additive may be provided as an admixture of the two compounds that may be added to water presently being treated with Ozone alone. In regards to the hypobromite ion scavenger additive, although hydantoins such as dimethylhydantoin (DMH) have been described in the present invention as being suitable hypobromite ion scavengers other additives containing imide and/or amide group similar to DMH may also be used to scavenge $OBr^-$ ion, provided they were present at sufficiently high concentrations.

An embodiment of the present invention includes a method for generating stable residual disinfectants during the ozonization of water comprising the step of carrying out the ozonization of water in the presence of bromide ions, silver ions and an effective amount of a hydantoin to thereby enhance the concentration of silver ions in the water while suppressing the catalytic decomposition reaction of Ozone with hypobromite ions.

A further embodiment of the present invention is an additive composition for generating secondary disinfectants during the ozonization of water comprising an admixture of bromide ions, silver ions and a hypobromite ion scavenger that converts hypobromite ions to biocidal, Ozone-stable derivatives thereof to thereby suppress the catalytic decomposition reaction of Ozone with hypobromite ions to eliminate or reduce the production the bromate to a safe level for human use.

Referring to FIGS. 4 and 5, FIG. 4 shows an embodiment of an apparatus of the present invention comprising a dispenser 10 having a housing 11 containing a compartment 12 therein. Located in compartment 12 is a source of DMH 13 and a bactericide comprising a silver ion donor such as silver bromide 14. A set of openings 15 allows water access to compartment 12 and to the source of DMH 13 and the silver bromide 14.

FIG. 5 shows an alternative embodiment of an apparatus of the present invention comprising a dispenser 16 having a first housing 17 with a compartment 18, a second housing 19 with a compartment 20, and a third housing 21 with a compartment 22 therein. Located in compartment 18 is a silver ion donor such as silver chloride 23, located in compartment 20 is a source of DMH 24, and located in compartment 22 is a bromide ion donor such as sodium bromide 25. A set of openings 26 allows water access to compartment 18 and to the silver chloride 23. A set of openings 27 allows water access to compartment 20 and the source of DMH 24. Similarly, a set of openings 28 allows water access to compartment 22 and the source of sodium bromide 25. Although FIGS. 4 and 5 show the use of the silver ion donor as comprising silver bromide and silver chloride, other types of silver ion donors and other alternative bactericides whose solubility can be changed in the presence of DMH can also be used. Similarly, although FIGS. 4 and 5 show the use of the bromide ion donor as comprising silver bromide and sodium bromide, other types of bromide ion donors may also be used.

In regards to the source of DMH 13, 24 of FIGS. 4 and 5, FIG. 5 shows source of DMH 24 in particles form with the aforementioned particles having an initial size that are larger than the size of opening 27 to prevent the DMH particles from escaping through openings 27. FIG. 4 shows the source of DMH 13 in tablet form. Various types of material including but not limited to microcrystalline cellulose (MCC) may be used as a binder in the formation of the DMH tablets which are tabletized with the metal ion donor so that both the DMH and the metal ion donor can be placed in the body of fluid to be treated.

It is noted that the preferred level of the DMH present in the body of water is between 5 and 50 ppm with the DMH and the source of silver cooperating to maintain a level of silver ions present in the amount of 1 to 3 ppb and/or alternatively cooperating to maintain a level of silver ions present to sustain a standard plate count at 35 degrees F. of less than 200 colonies per milliliter. The level of the DMH in the body of water however may be higher than 50 ppm.

The present invention includes a method of treating an ozonized body of water in the presence of bromide ions to kill microorganisms by enhancing the metal ions concentration while eliminating or reducing the production bromate, the method comprising the steps of placing the dispenser 10, 16 containing the source of DMH 13, 24, a silver ion donor 14, 23, and a bromide ion donor 14, 25 in the body of water and allowing water that has been treated with ozone to come into contact with the source of DMH 13, 24, the silver ion donor 14, 23, and the bromide ion donor 14, 25 to periodically release DMH, silver ions, and bromide ions into the body of water. As the DMH is released into the body of water, the DMH is carried to the silver ion donor 14, 23 and the bromide ion donor 14, 25 and interacts with the silver ion donor 14, 23 and the bromide ion donor 14, 25 to increase the solubility of the silver ions. That is, the DMH functions to allow for the release of more silver ions into the body of water and/or maintain the silver ions concentration in the body of water at a higher of level than if the silver ion donor 14, 23 were used alone in the body of water while suppressing the conversion of the bromide ions by the Ozone in the water to a bromate to render the water for human use.

The present invention also includes a method of treating a body of water to kill microorganisms by maintaining an effective concentration of biocides, the method comprising the steps of (1) treating the body of water with ozone; (2) adding a silver ion donor 14, 23 to the body of water; (3) adding a source of bromide 14, 25 to the body of water and (4) adding a concentration 5,5-dimethylhydantoin (DMH) 13, 24 to the body of water to interact with the silver ion donor 14, 23 to maintain a silver ion concentration effective to kill microorganisms while suppressing the interaction between the ozone and the bromide ions to eliminate or reduce the production a bromate to a safe level for human use. The aforementioned method can also include the steps of (5) adding silver chloride 14, 21 to the body of water; (6) adding silver bromide to the body of water (7) treating a body of recreational water for at least partial human immersion therein; (8) placing a dispenser 10, 16 containing both the silver salt 14, 21 and the 5,5-dimethylhydantoin 13, 22 in the body of water and allowing water to come into contact with both the silver salt 14, 21 and the 5,5-dimethylhydantoin 13, 22; and (9) adding silver chloride to the body of water on a carrier of limestone.

I claim:

1. A dispenser for killing microorganisms in a body of water that has been treated with ozone in the presence of bromide ions comprising:

a first housing having a water accessible compartment, the contents of the first housing consisting essentially of 5,5-dimethylhydantoin for releasing 5,5-dimethylhydantoin as a hypobromite ion scavenger when contacted by the body of water;

a second housing having a water accessible compartment containing a silver ion donor for releasing metal ions when contacted by the body of water; and a third housing having a water accessible compartment, the contents of the third housing consisting essentially of sodium bromide for releasing bromide ions when contacted by the body of water.

2. The dispenser of claim 1 wherein the silver ion donor comprises silver bromide.

3. The dispenser of claim 1 wherein the 5,5-dimethylhydantoin and the silver ion donor are in tablet form.

4. The dispenser of claim 1 wherein the silver ion donor comprises silver chloride.

5. The dispenser of claim 1 wherein the first housing, the second housing, and the third housing are located in a dispenser having a set of openings for the ingress and egress of water into the compartments in the dispenser.

* * * * *